United States Patent [19]

Gaines, Jr.

[11] Patent Number: 4,950,269
[45] Date of Patent: Aug. 21, 1990

[54] SPINAL COLUMN FIXATION DEVICE

[75] Inventor: Robert W. Gaines, Jr., Columbia, Mo.

[73] Assignee: AcroMed Corporation, Cleveland, Ohio

[21] Appl. No.: 206,007

[22] Filed: Jun. 13, 1988

[51] Int. Cl.⁵ .............................................. A61F 5/01
[52] U.S. Cl. ....................... 606/61; 128/69; 128/83
[58] Field of Search .......... 128/92 Z, 92 ZZ, 92 ZW, 128/92 ZY, 92 YV, 92 YF, 92 YE, 92 YM, 69, 75, 83; 403/354, 359, 397–399, 395, 344; 248/71, 74.1, 74.2, 73, 74, 3, 316.7, 74.4, 62, 65; 24/459, 542, 462, 486; 411/355, 362, 363, 373, 375, 522, 523, 529; 606/60, 61, 62, 65, 72

[56] References Cited

U.S. PATENT DOCUMENTS

| | | | |
|---|---|---|---|
| 3,286,963 | 11/1966 | Bergman | 248/74.1 |
| 4,557,447 | 12/1985 | Combe | 248/74.1 |
| 4,601,450 | 7/1986 | Lindquist | 248/71 |
| 4,648,388 | 3/1987 | Steffee | 128/69 |
| 4,653,481 | 3/1987 | Howland et al. | 128/69 |
| 4,783,029 | 11/1988 | Geppert et al. | 248/74.1 |

FOREIGN PATENT DOCUMENTS 2649042 9/1978 Fed. Rep. of Germany ........ 128/69
3614101 10/1987 Fed. Rep. of Germany .

Primary Examiner—Richard J. Apley
Assistant Examiner—H. N. Flaxman
Attorney, Agent, or Firm—Tarolli, Sundheim & Covell

[57] ABSTRACT

An apparatus for connecting vertebrae including a rod and a fastener for connecting the rod with a vertebra of a spinal column. The fastener includes a screw having a threaded portion for connection with the vertebra. The screw has a head connected to one end of the threaded portion. The head includes a bight portion and a pair of spaced apart resiliently deflectable legs extending from the bight portion. The pair of legs and the bight portion define a cavity in the screw head. The rod is receivable in the cavity in the screw head. A cap is receivable on the pair of legs and deflects the pair of legs to clamp around the portion of the rod received in the cavity in the screw head. The cap is retained on the screw so that movement of the rod relative to the screw is blocked.

14 Claims, 4 Drawing Sheets

SPINAL COLUMN FIXATION DEVICE

BACKGROUND OF THE INVENTION

1. Field of the Invention

The present invention relates to a fixation device for a spinal column. In particular, the present invention relates to a fastener for connecting a member which extends between vertebrae to one of the vertebrae.

2. Description of the Prior Art

Surgically implantable fixation devices for connecting vertebrae of a deformed or degenerated spinal column are known. U.S. Pat. No. 4,648,388 discloses one such fixation device for interconnecting at least a pair of vertebrae of a spinal column. The fixation device includes an elongate rod connected with the vertebrae. A screw is threaded into a vertebra and has a portion extending from the vertebra. A clamp is placed on the portion of the screw extending from the vertebra. The clamp has a contractable opening for receiving a portion of the rod. A nut is threaded onto the screw against the clamp to contract the opening of the clamp around the portion of the rod. Friction and/or a mechanical interlock between the clamp and the portion of the rod prevents movement of the rod relative to the clamp and screw and, thus, the vertebra.

German Patent No. 26 49 042 discloses a screw having a threaded portion for connection with a vertebra The screw has an intermediate portion fixed to the threaded portion and a pair of legs extending from the intermediate portion. The intermediate portion and pair of legs define a cavity in the screw for receiving a portion of a threaded rod. A pair of nuts are threaded onto the rod and engage the screw from axially opposite directions. The nuts are tightened against the screws to block movement of the rod relative to the screw.

SUMMARY OF THE INVENTION

The present invention is directed to a spinal column fixation device including a fastener and a connecting member in the form of an elongate rod. The fastener includes a screw having a threaded portion for connection with a vertebra of the spinal column and a bight portion fixed to the threaded portion of the screw. A pair of spaced apart and resiliently deflectable legs extend from the bight portion. The pair of legs and the bight portion have surfaces which define a cavity in the screw for receiving a portion of the rod. A cap has a cavity for receiving the pair of legs of the screw and is retained on the pair of legs to block relative movement between the rod and the screw.

A respective projection extends transversely from each one of the pair of legs in opposite directions. The projections are received in the cavity in the cap to block movement of the cap relative to the screw in a direction transverse to the direction in which the rod extends. The cavity in the cap has a width slightly smaller than the width between the outermost extent of the projections to deflect the pair of legs relatively toward one another when the projections are received in the cavity in the cap. Deflection of the legs toward one another clamps the rod between the pair of legs and the bight portion. The cap also has a recess extending from the cavity for receiving an end portion of one of the pair of legs to block movement of the cap relative to the screw in a direction substantially parallel to the longitudinal central axis of the rod.

In another embodiment of the present invention, the rod has a first portion with a cross section taken in a plane extending perpendicular to the longitudinal central axis of the rod of a first width. The rod also has a second portion with a cross section taken in a plane extending perpendicular to the longitudinal central axis of the rod of a second width which is greater than the first width. A surface of the screw projects into a recess defined by the first portion of the rod and engages the second portion of the rod to block movement of the rod relative to the screw in a direction substantially parallel to the longitudinal central axis of the rod.

BRIEF DESCRIPTION OF THE DRAWINGS

Further features of the present invention will become apparent to those skilled in the art to which the present invention relates from reading the following specification with reference to the accompanying drawings, in which.

DESCRIPTION OF PREFERRED EMBODIMENTS

Figure 1:
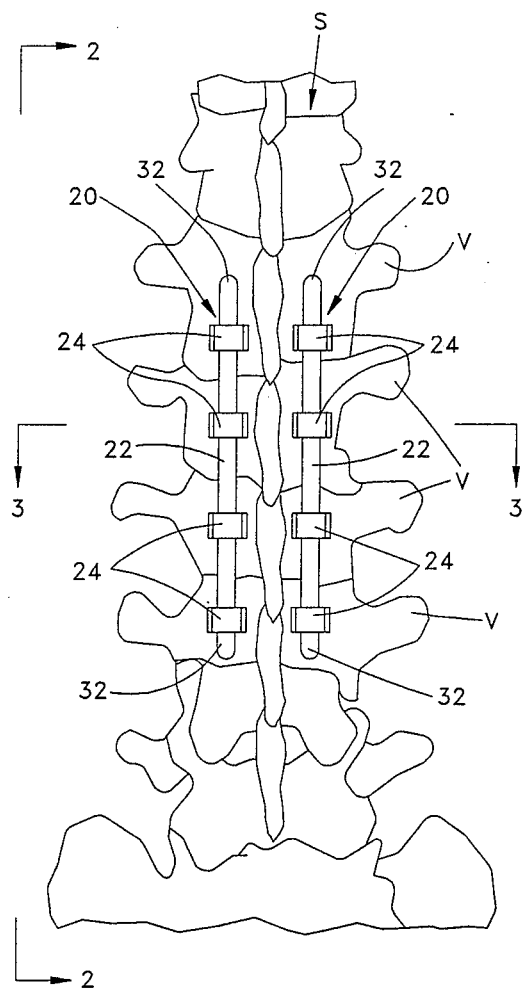
FIG. 1 is a view of a pair of fixation devices according to the present invention connected to a portion of a spinal column.

A pair of surgically implantable fixation devices 20 (FIG. 1) connect together vertebrae V of a human spinal column S and maintain the vertebrae in a spaced relationship. Each fixation device 20 includes an elongate rod 22 and a plurality of fasteners 24 connecting the rod 22 with the vertebrae V. It will be apparent that the rod 22 may be of that different lengths and that different numbers of fasteners 24 may be used to connect together more or less than the four vertebrae V which are connected together in FIGS. 1 and 2.

Figure 2:
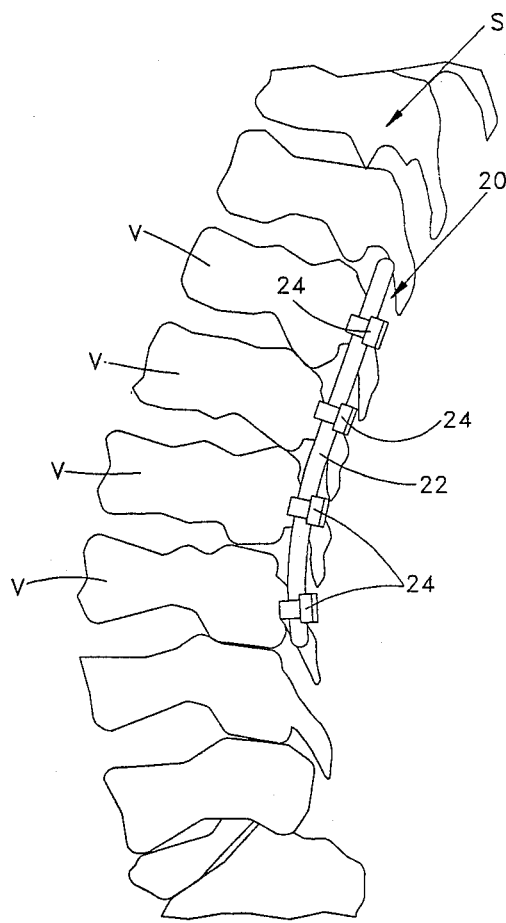
FIG. 2 is a view of one of the fixation devices of FIG. 1 connected to the portion of the spinal column, taken approximately along line 2—2 in FIG. 1.
Figure 3:
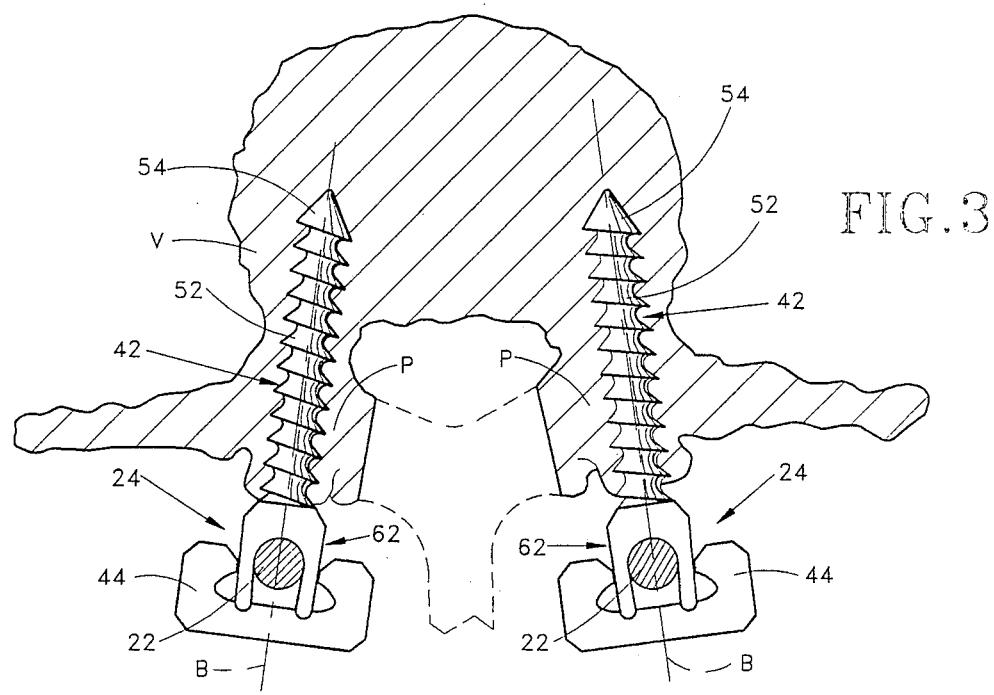
FIG. 3 is an enlarged cross sectional view of the fixation devices of FIG. 1 connected to a vertebra, taken approximately along line 3—3 in FIG. 1.

In a first embodiment of the present invention, each rod 22 has a longitudinal central axis A (FIG. 4) and a generally circular cross section which is relatively constant for the length of the rod. The ends 32 (FIGS. 1 and 2) of the rod 22 are hemispherical. The rod 22 is made of a material which is compatible with human tissue, such as surgical grade titanium or stainless steel. The rod 22 is relatively rigid but is bendable to conform to a desired curvature of the spinal column S, as illustrated in FIG. 2. The length of each rod 22 is selected to be sufficiently long enough to span the distance of the desired number of vertebrae V to be connected together Each fastener 24 connects the rod 22 with one of the vertebrae V. Each fastener 24 includes a screw 42 (FIGS. 3 and 4) and a cap 44. The screw 42 is made of a material that is compatible with human tissue such as surgical grade stainless steel. The screw 42 includes a threaded portion 52 for threaded connection with a pedicle P of a vertebra V, as illustrated in FIG. 3. One axial end portion 54 of the threaded portion 52 is pointed. When the screw 42 is rotated about its longitudinal central axis B in an opening in the vertebra V, the threaded portion 52 advances the screw 42 into the vertebra, as is known. The screw 42 may be rotated about its longitudinal central axis B by a known open end wrench (not shown).

The screw 42 also includes a head 62 which extends from and is fixed to the other axial end of the threaded portion 52. The head 62 includes a bight portion 64 located adjacent the threaded portion 52. A pair of resilient deflectable legs 66, 68, (FIG. 4) extend from the bight portion 64 of the screw 42 in a direction generally parallel to the longitudinal central axis B (FIG. 3) of the screw. However, it will be apparent that the screw 42 can be formed so the legs 66, 68 extend at an angle relative to the longitudinal central axis of the screw.

Figure 4:
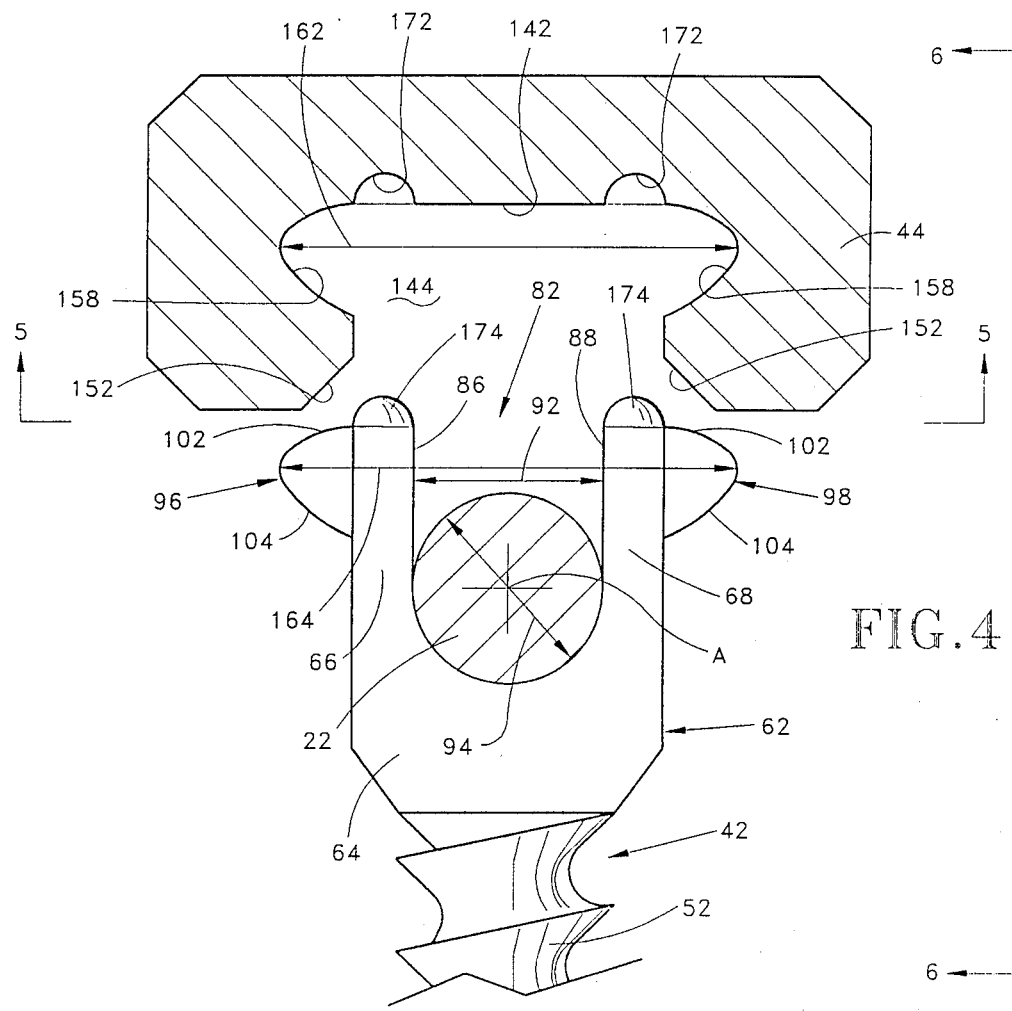
FIG. 4 is an enlarged exploded cross sectional view of a portion of one of the fixation devices of FIG. 3.

A cavity 82 (FIG. 4) is formed in the screw 42 between the bight portion 64 and facing surfaces 86, 88 of the pair of legs 66, 68, respectively. A portion of the rod 22 is receivable in the cavity 82 in the screw 42, as illustrated in FIG. 4. The cavity 82 in the screw 42 has a width 92 which is substantially equal to the diameter 94 of the cross section of the rod 22 taken in a plane extending perpendicular to the longitudinal central axis A of the rod. The portion of the rod 22 received in the cavity 82, thus, engages the bight portion 64 and the facing surfaces 86, 88 of the pair of legs 66, 88.

A projection 96, 98 extends transversely outwardly from each one of a pair of legs 66, 68, respectively. The projections 96, 98 extend in a direction away from one another. Each projection 96, 98 has a cam surface 102 located adjacent the end of the screw 42. Each projection 96, 98 also has a retaining surface 104 facing in a direction away from the cam surface 102. Each projection 96, 98 extends substantially the entire length 112 of the head 62 of the screw 42, as illustrated in FIG. 6.

The cap 44 is retained on the screw 42 to keep the rod 22 within the cavity 82 of the screw. The cap 44 has a generally C-shaped cross section, as illustrated in FIG. 4, and is deflectable to the configuration illustrated in FIG. 7. The cap 44 is made from a material which is compatible with human tissue, such as a surgical grade stainless steel. The length 132 (FIG. 6) of the cap 44 is greater than the length 112 of the head 62 of the screw 42. An interior surface 142 (FIG. 4) of the cap 44 defines a cavity 144 in the cap. The pair of legs 66, 68 on the screw 42 are receivable in the cavity 144 in the cap 44.

Figures 6, 7:
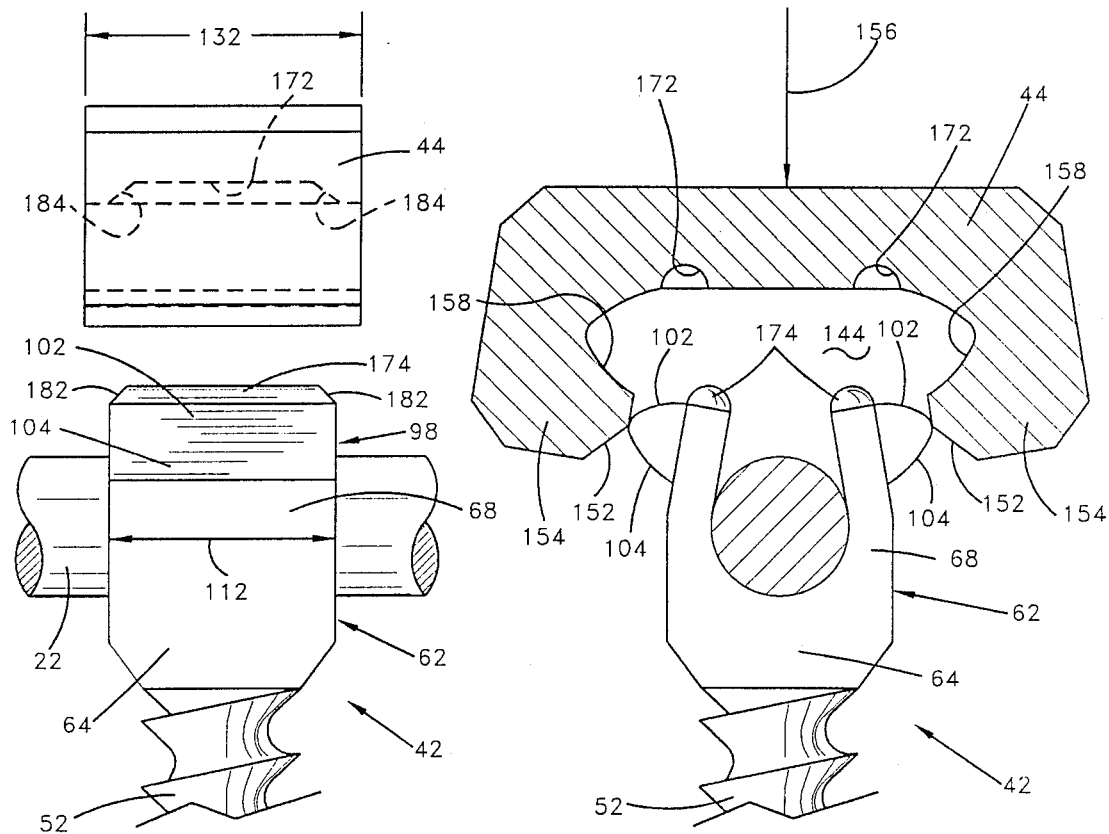
FIG. 6 is a side view of the fixation device of FIG. 4, taken approximately along line 6—6 in FIG. 4.
FIG. 7 is a view similar to FIG. 4 illustrating the parts in different positions.

The cap 44 is manually forced onto the pair of legs 66, 68 of the screw 42 toward the bight portion 64 of the screw in the direction indicated by the arrow 156 (FIG. 7). The cap 44 may be held manually when it is forced onto the screw or may be held by a suitable tool (not shown). The cap 44 has a pair of angled end surfaces 152 located at the entrance to the cavity 144 in the cap. Each angled end surface 152 engages a respective cam surface 102 of the projections 96, 98 as is illustrated in FIG. 7, to deflect the pair of legs 66, 68 of the screw 42 toward one another and end portions 154 of the cap 44 away from one another and to expand the opening to the cavity 144 so the cap can receive the pair of legs.

As the cap 44 is forced further onto the pair of legs 66, 68 of the screw 42, from the position illustrated in FIG. 7 to the position illustrated in FIG. 3, the retaining surfaces 104 of the projections 96, 98 enter the cavity 144 in the cap. The retaining surfaces 104 engage surfaces 158 of the cavity 144 adjacent the opening to the cavity 144. During movement of the cap 44 from the position illustrated in FIG. 7 to the position illustrated in FIG. 3, the pair of legs 66, 68 resiliently deflect away from one another and the end portions 154 of the cap resiliently deflect toward one another. The retaining surfaces 104 engage the surfaces 158 of the cavity 144 to resist removal of the cap 44 from the legs 66, 68 of the screw 42 in a direction substantially parallel to the direction the legs extend. The cap 44, thus, retains the rod 22 within the cavity 82 in the screw 42 to block the rod from moving relative to the screw in a direction transverse to the longitudinal central axis A of the rod.

The width 162 (FIG. 4) of the cavity 144 in the cap 44 is slightly smaller than the width 164 across the outermost extent of the projections 96, 98. Thus, the pair of legs 66, 68 are maintained slightly deflected toward one another, as illustrated in FIG. 3, from the free state of their initial position illustrated in FIG. 4. The slight deflection of the pair of legs 66, 68 presses the rod 22 against the bight portion 64 of the screw 42. Thus, the head 62 of the screw 42 clamps about the portion of the rod 22 received in the cavity 82 in the screw 42. Friction between the head 62 of the screw 42 and the rod 22 prevents rotation of the rod in the cavity 82 of the screw and axial movement of the rod relative to the screw in a direction substantially parallel to the longitudinal central axis A of the rod.

Figure 5:
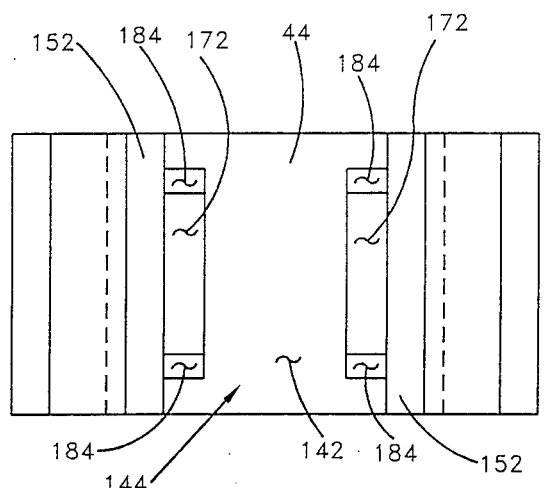
FIG. 5 is a view of a cap of the fixation device of FIG. 4, taken approximately along line 5—5 in FIG. 4.

The cap 44 has a pair of elongate recesses 172 (FIGS. 4-7) extending into the cap 44 from the cavity 144. The length of the recesses 172 is less than the length 132 (FIG. 6) of the cap 44 and slightly greater than the length 112 of the head 62 of the screw 42. The recesses 172 are centered lengthwise in the cap 44, as viewed in FIGS. 5 and 6. An end portion 174 (FIGS. 4, 6 and 7) of each of the pair of legs 66, 68 of the screw 42 is receivable in a respective recess 172 in the cap 44. End surfaces 182 of the end portions 174 of the legs 66, 68 are engageable with end surfaces 184 of the recesses 172 to block movement of the cap 44 relative to the screw 42 in a direction substantially parallel to the longitudinal central axis A of the rod 22 when the rod is received in the cavity 82 in the screw.

In a second embodiment of the present invention, a fixation device 202 (FIG. 8) includes a modified rod 212 receivable in a cavity 214 (FIG. 10) in a modified screw 216. The fixation device 202 (FIG. 8) connects together vertebrae of a spinal column to maintain the vertebrae in a spaced relationship. A cap 222, which is identical to the cap 44 described above for the first embodiment, is receivable on the screw 216. The fixation device 202 provides increased resistance to movement of the rod 212 relative to the screw 216 in a direction substantially parallel to the axis C of the rod.

Figure 8:
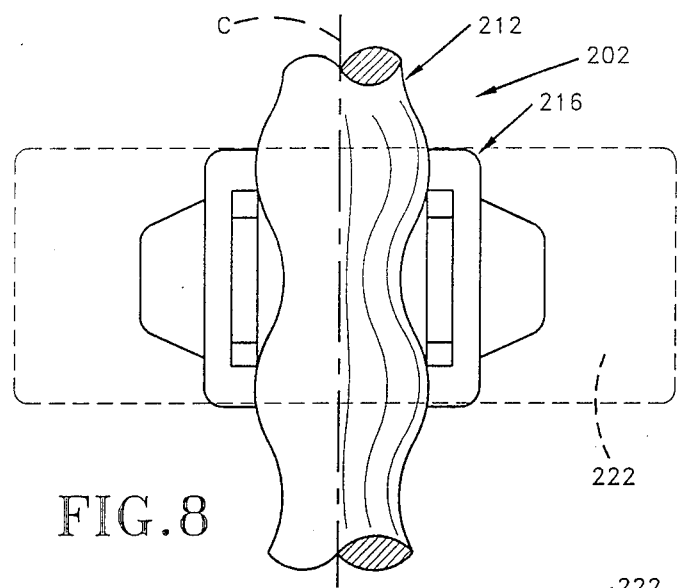
FIG. 8 is a view of a fixation device according to another embodiment of the present invention.
Figure 9:
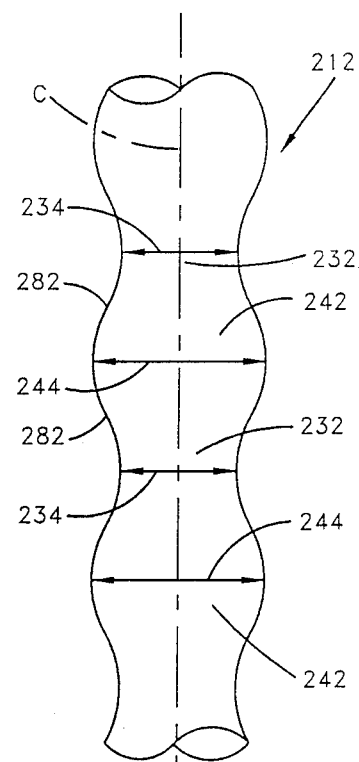
FIG. 9 is a view of a rod of the fixation device of FIG. 8.

The rod 212 has an undulating exterior surface, as viewed in FIGS. 8 and 9. The rod 212 has a first portion 232 with a circular cross section of a first diameter 234 taken in a plane perpendicular to the longitudinal central axis C of the rod. The rod 212 has a second portion 242 with a circular cross section taken in a plane perpendicular to the longitudinal central axis C of the rod of a second diameter 244. The second diameter 244 is greater than the first diameter 234. The rod 212 is made up of a plurality of identical sections having the first portion 232 and the second portion 242 alternating and extending axially in both directions. The first portion 232, thus, defines a recess in the rod 212 extending axially between adjacent second portions 242. The rod 212 is relatively rigid but is bendable to conform to a desired curvature of a spinal column.

Figure 10:
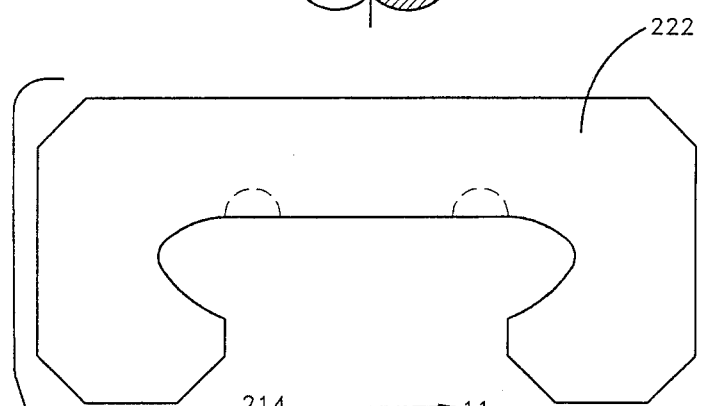
FIG. 10 is an enlarged exploded view of the fixation device of FIG. 8, taken approximately along line 10—10 in FIG. 8.
Figure 10:
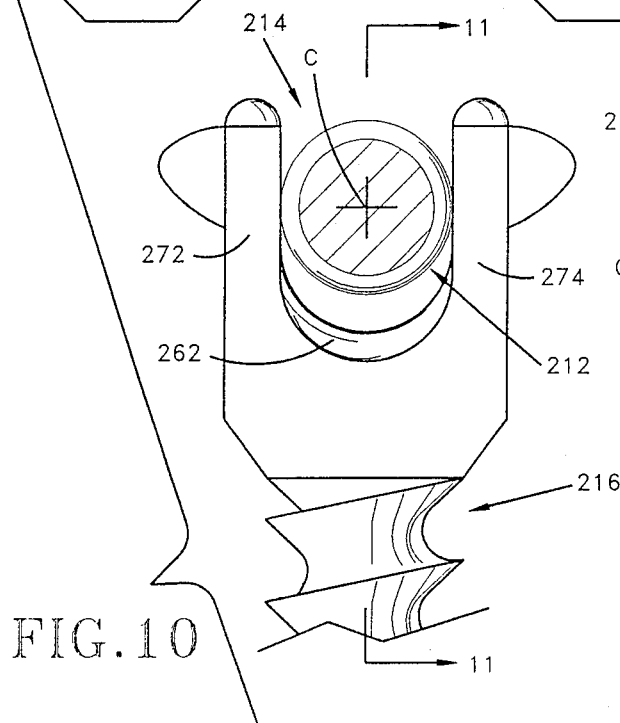
Figure 11:
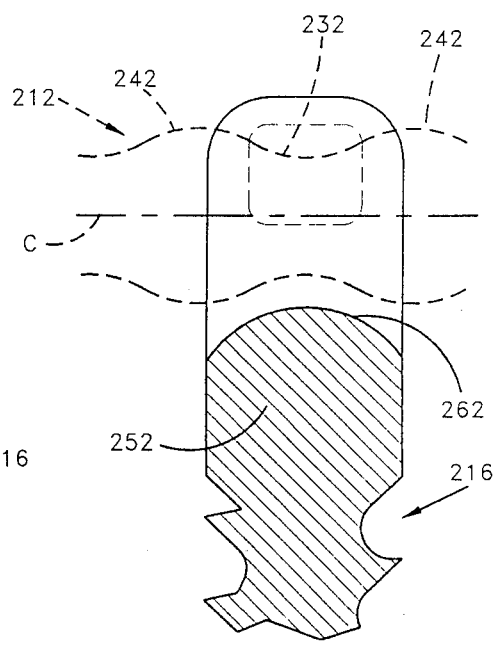
FIG. 11 is a cross sectional view of a screw of the fixation device of FIG. 10, taken approximately along line 11—11 in FIG. 10.

The screw 216, illustrated in FIGS. 10 and 11, is similar to the screw 22 described above but has been modified so that a bight portion 252 of the screw 216 has a convex surface 262 partially defining the cavity 214. The convex surface 262 projects outwardly from the bight portion 252 of the screw 216 into the cavity 214. The convex surface 262 is receivable in the recess in the rod 212 defined by the first portion 232, as illustrated in FIG. 11.

When the cap 222 is received on the screw 216, the clamping action of legs 272, 274 of the screw around the rod 212 is similar to the clamping described above between the rod 22 and screw 42 of the first embodiment. This clamping prevents the rod 212 from moving relative to the screw 216 in a direction transverse to the longitudinal central axis C of the rod. The convex surface 262 extending into the recess in the rod 212 defined by the first portion 232 is engageable with a second portion 242 of the rod to block relative movement between the rod 212 and the screw 216 in a direction substantially parallel to the longitudinal central axis C of the rod. The convex surface 262 extending into the recess in the rod 212 defined by the first portion 232, thus, acts in addition to the clamping force of the legs 272, 274 around the periphery of the rod 212 to provide positive blocking of movement of the rod in a direction parallel to the axis C of the rod relative to the screw 216. The convex surface 262 extending into the recess in the rod 212 defined by the first portion 232 also reduces the criticality of the clamping force that the legs 272, 274 have to exert against the rod to block movement of the rod in a direction along its longitudinal central axis C.

The portions 232, 242 are blended into one another by a blend radius 282 extending axially between the adjacent portions. This serves to reduce any stress risers which could result from sudden changes in the diameters 234, 244 of the rod 212. It will be understood that the diameters 234, 244 of the rod illustrated in FIG. 8 are exaggerated for example purposes. In actual use, the diameters 234, 244 of the rod 212 preferably differ only 1 to 2 millimeters. For example, the diameter 234 may be five millimeters and the diameter 244 may be seven millimeters, or the diameter 234 may be six millimeters and the diameter 244 may be seven millimeters if a stronger rod is required.

From the above description of a preferred embodiment of the invention, those skilled in the art will perceive improvements, changes and modifications. Such improvements, changes and modifications within the skill of the art are intended to be covered by the appended claims.

Having described preferred embodiments of the invention, I claim:

1. A spiral column fixation device comprising:
   a bio-compatible screw including a threaded portion for connection with a vertebra of a spinal column, a bight portion fixed to said threaded portion and a pair of spaced apart resiliently deflectable legs extending from said bight portion, said pair of legs and said bight portion having surfaces defining a cavity in said screw;
   a rod sized for connection with the spiral column of a patient including a portion receivable in the cavity in said screw;
   a cap receivable on said pair of legs of said screw;
   means for retaining said cap on said screw to block movement of said rod from the cavity in said screw; and
   wherein the fixation device is of a size and shape adapted for use with the spinal column of a patient.

2. The spinal column fixation device set forth in claim 1 wherein said retaining means includes surface means defining a cavity in said cap and a projection extending transversely from one of said pair of legs, said projection being receivable in the cavity in said cap to block movement of said cap relative to said screw in a direction substantially parallel to the direction in which said one of said pair of legs extends.

3. The spinal column fixation device set forth in claim 1 wherein said retaining means includes surface means defining a recess in said cap for receiving a portion of one of said pair of legs to block movement of said cap relative to said screw in a direction substantially parallel to the direction said rod extends when said rod is received in the cavity in said screw.

4. The spinal column fixation device set forth in claim 1 further including means for deflecting at least one of said pair of legs to clamp said portion of said rod between said pair of legs and said bight portion to block relative movement between said rod and said screw.

5. A spinal column fixation device comprising:
   a bio-compatible screw including a threaded portion for connection with a vertebra, a bight portion fixed to said threaded portion and a pair of spaced apart resiliently deflectable legs extending from said bight portion, said pair of legs and said bight portion having surfaces defining a cavity in said screw;
   a rod including a portion receivable in the cavity in said screw;
   means for deflecting at least one of said pair of legs to clamp said portion of said rod between said pair of legs and said bight portion to block relative movement between said rod and said screw; and
   wherein the fixation device is of a size and shape adapted for use with the spinal column of a patient.

6. A spinal column fixation device set forth in claim 5 wherein said deflecting means includes a cap having surface means defining a cavity in said cap for receiving said pair of legs and a pair of projections, each of said projections extending transversely from a respective one of said pair of legs in a direction away from one another, said surface means defining the cavity in said cap having a width less than the width between the outermost extent of said projections for pressing said pair of legs relatively toward one another when said projections are received in the cavity in said cap.

7. A spinal column fixation device set forth in claim 6 wherein each of said projections includes a cam surface and said cap includes surfaces for engaging a respective one of said cam surfaces to expand said cap over said projections and deflect said pair of legs relatively toward one another from an initial free state position as said cap is moved to a first position relatively toward said bight portion of said screw, said projections being received in the cavity in said cap when said cap is moved to a second position from the first position in a direction further toward said bight portion of said screw to block movement of said cap relative to said screw in a direction substantially parallel to the direction in which said pair of legs extend.

8. The spinal column fixation device comprising:
an elongate rod including a first portion having a cross section taken in a plane extending perpendicular to the longitudinal central axis of said rod of a first width and a second portion axially adjacent said first portion and having a cross section taken in a plane extending perpendicular to the longitudinal central axis of said rod of a second width greater than said first width so said first portion defines a recess in said rod;
a bio-compatible screw including a threaded portion for connection with a vertebra and a head integral with to said threaded portion, said head including surface means defining a cavity for receiving said first portion of said rod;
means for blocking movement of said first portion of said rod relative to said head of said screw in a direction transverse to the longitudinal central axis of said rod when said rod is received in said cavity in said screw;
a portion of said surface means defining the cavity in said head of said screw being extendable into the recess in said rod and being engageable with said second portion of said rod to block movement of said rod relative to said fastener in a direction parallel to the longitudinal central axis of said rod; and
wherein the fixation device is of a size and shape adapted for use with the spinal column of a patient.

9. The spinal column fixation device set forth in claim 8 wherein said blocking means includes a cap having surface means defining a cavity in said cap for receiving a portion of said head of said screw and means for retaining said cap on said head of said screw.

10. The spinal column fixation device set forth in claim 9 wherein said retaining means includes surface means defining a recess in said cap for receiving a portion of said head to block movement of said cap relative to said screw in a direction substantially parallel to the direction said rod extends when said rod is received in the cavity in said screw.

11. The spinal column fixation device set forth in claim 8 further including means for deflecting a portion of said head of said screw to clamp said first portion of said rod to block movement of said rod relative to said screw.

12. An apparatus comprising:
a screw including a threaded portion for connection with a vertebra of a spinal column, a bight portion fixed to said threaded portion and a pair of spaced apart resiliently deflectable legs extending from said bight portion, said pair of legs and said bight portion having surfaces defining a cavity in said screw;
a rod including a portion receivable in the cavity in said screw;
a cap receivable on said pair of legs of said screw; and
means for retaining said cap on said screw to block movement of said rod from the cavity in said screw, wherein said rod includes a first portion with a cross section in a plane extending perpendicular to the longitudinal central axis of said rod of a first width and a second portion with a cross section in a plane extending perpendicular to the longitudinal central axis of said rod of a second width greater than said first width, said first portion being receivable in the cavity in said screw and defining a recess in said rod, and said retaining means further includes a projection on said screw extending into the cavity in said screw and into the recess in said rod for engaging said second portion of said rod to block movement of said rod relative to said screw in a direction substantially parallel to the longitudinal central axis of said rod.

13. An apparatus comprising:
a screw including a threaded portion for connection with a vertebra, a bight portion fixed to said threaded portion and a pair of spaced apart resiliently deflectable legs extending from said bight portion, said pair of legs and said bight portion having surfaces defining a cavity in said screw;
a rod including a portion receivable in the cavity in said screw; and
means for deflecting at least one of said pair of legs to clamp said portion of said rod between said pair of legs and said bight portion to block relative movement between said rod and said screw, including a cap having surface means defining a cavity in said cap for receiving said pair of legs and a pair of projections, each of said projections extending transversely from a respective one of said pair of legs in a direction away from one another, said surface means defining the cavity in said cap having a width less than the width between the outermost extent of said projections for pressing said pair of legs relatively toward one another when said projections are received in the cavity in said cap, said cap further including surface means defining a recess in said cap for receiving a portion of one of said pair of legs to block movement of said cap relative to said screw in a direction substantially parallel to the direction that said rod extends when said rod is received in the cavity in said screw.

14. An apparatus comprising:
an elongate rod including a first portion having a cross section taken in a plane extending perpendicular to the longitudinal central axis of said rod of a first width and a second portion axially adjacent said first portion and having a cross section taken in a plane extending perpendicular to the longitudinal central axis of said rod of a second width greater than said first width so said first portion defines a recess in said rod;
a screw including a threaded portion for connection with a vertebra and a head fixed to said threaded portion, said head including surface means defining a cavity for receiving said first portion of said rod;
means for blocking movement of said first portion of said rod relative to said head of said screw in a direction transverse to the longitudinal central axis of said rod when said rod is received in said cavity in said screw; and
a portion of said surface means defining the cavity in said head of said screw being extendable into the recess in said rod and being engageable with said second portion of said rod to block movement of said rod relative to said fastener in a direction parallel to the longitudinal central axis of said rod;
wherein said blocking means includes a cap having surface means defining a cavity in said cap for receiving a portion of said head of said screw and means for retaining said cap on said head of said screw, and said retaining means includes a projection extending transversely from said head and being receivable in the cavity in said cap to block movement of said cap relative to said screw in a direction transverse to the direction in which said rod extends when said rod is received in the cavity in the head.

* * * * *

UNITED STATES PATENT AND TRADEMARK OFFICE
CERTIFICATE OF CORRECTION

PATENT NO.  : 4,950,269

DATED       : August 21, 1990

INVENTOR(S) : Robert W. Gaines, Jr.

It is certified that error appears in the above-identified patent and that said Letters Patent is hereby corrected as shown below:

Column 5, Line 68, Claim 1, change "spiral" to --spinal--.

Signed and Sealed this

Tenth Day of March, 1992

Attest:

HARRY F. MANBECK, JR.

*Attesting Officer*          *Commissioner of Patents and Trademarks*